(12) United States Patent
Laherty et al.

(10) Patent No.: US 7,104,980 B1
(45) Date of Patent: Sep. 12, 2006

(54) CATHETERIZATION ASSIST DEVICE AND METHOD OF USE

(76) Inventors: Dennis M Laherty, 12281 Lesley St., Garden Grove, CA (US) 92840; Nancy A Laherty, 4528 Jan Dr., Carmichael, CA (US) 95608

( * ) Notice: Subject to any disclaimer, the term of this patent is extended or adjusted under 35 U.S.C. 154(b) by 232 days.

(21) Appl. No.: 10/759,477

(22) Filed: Jan. 16, 2004

(51) Int. Cl.
*A61M 25/01* (2006.01)
*A61M 25/02* (2006.01)
*A61M 25/04* (2006.01)
*A61M 25/06* (2006.01)
*A61M 25/08* (2006.01)
*A61M 25/09* (2006.01)
*A61M 25/82* (2006.01)
*A61M 25/85* (2006.01)
*A61M 25/88* (2006.01)
*A61M 25/95* (2006.01)
*A61M 25/98* (2006.01)
*A61M 25/00* (2006.01)
*A61M 27/00* (2006.01)
*A61B 5/00* (2006.01)

(52) U.S. Cl. .................... 604/528; 604/523; 604/544; 600/585

(58) Field of Classification Search ............... 600/574, 600/585; 604/327–330
See application file for complete search history.

(56) References Cited

U.S. PATENT DOCUMENTS

| | | | |
|---|---|---|---|
| 3,815,581 A * | 6/1974 | Levin | 600/574 |
| 4,023,560 A | 5/1977 | Cade et al. | |
| 4,834,711 A | 5/1989 | Greenfield et al. | |
| 4,911,698 A * | 3/1990 | Wapner | 604/329 |
| 5,045,078 A | 9/1991 | Asta | |
| 5,084,036 A | 1/1992 | Rosenbaum | |
| 5,653,700 A | 8/1997 | Byrne et al. | |
| 6,461,340 B1 * | 10/2002 | Lenker et al. | 604/385.17 |
| 6,544,240 B1 | 4/2003 | Borodulin et al. | |
| 2001/0020162 A1 | 9/2001 | Mosel et al. | |

* cited by examiner

*Primary Examiner*—Tatyana Zalukaeva
*Assistant Examiner*—Melanie J Hand
(74) *Attorney, Agent, or Firm*—Baker & Daniels LLP

(57) ABSTRACT

A device and method of using the device to assist in inserting a catheter in a female. The device includes a main body portion configured to be placed adjacent the pubic bone of a female, a pair of legs extending downwardly from the main body portion, a slot located between the legs, and a flange extending longitudinally along each of the legs. The flanges may extend along inner sides of the legs adjacent the slot. The device may also include a catheter guide formed at the upper end of the slot. The catheter guide may include a curved surface that extends along a portion of the main body member and each of the legs. The device may further include a gripping portion at an upper end of the main body. In one embodiment, the main body defines a plane, and the legs extend outwardly at an angle to the plane. A portion of the flanges may extend substantially transverse to the plane defined by the main body.

26 Claims, 5 Drawing Sheets

CATHETERIZATION ASSIST DEVICE AND METHOD OF USE

BACKGROUND OF THE INVENTION

This invention relates to a catheterization assist device, and more particularly, to a catheterization assist device and method that may be used by a female for self-catheterization.

The use of catheters is well known to alleviate a variety of medical conditions that prevent the normal evacuation of the bladder. The catheter is a tube or device that can be inserted in the urethra of either a male or female and threaded into the bladder to permit the bladder to be emptied or evacuated therethrough. The insertion of catheters can be cumbersome, and in particular, the insertion of catheters in female patients may be complicated by the need to expose the urethra for insertion of the catheter. Additionally, some medical conditions require intermittent catheterization wherein a female patient may have to catheterize herself. In some instances, it may be difficult for the patient to expose and see the urethra and then to properly align the catheter with the urethra.

One prior art device is shown in U.S. Pat. No. 4,023,560 to Cade et al. This device is designed for obtaining a clean urine sample from a female, but it is also indicated that the device may be used to assist in inserting a catheter. The device disclosed by Cade et al. includes a generally U-shaped portion and leg portions extending transverse from the U-shaped portion. The U-shaped portion is designed for insertion into the vagina of a patient while the leg portions spread the labia. Cade et al. does not disclose that the device may be used by a female for self-catheterization.

Another prior art device is disclosed in U.S. Pat. No. 5,045,078 to Asta. The device disclosed by Asta is designated for use by a female for self-catheterization, and includes a vaginal insert and a catheter guide having a handle portion and an adjustment mechanism with an alignment hole. As with the device disclosed by Cade et al., use of the device disclosed by Asta requires inserting a significant portion of the device into the vagina of a patient, and furthermore, requires the patient to make adjustments of the adjustment mechanism to align the alignment hole with the urethra. The device in Asta does not assist in spreading the labia and the adjustment mechanism may impair vision of the urethra.

Another device for use in insertion of a catheter is disclosed in U.S. Pat. No. 4,834,711 to Greenfield et al. The device disclosed by Greenfield et al. is primarily designed to lubricate and disinfect a catheter to be inserted.

Another prior art device is disclosed in U.S. Pat. No. 5,084,036 to Rosenbaum. The device disclosed by Rosenbaum is suggested for use in self-catheterization of a female and includes a body portion, and a locating member with a handle portion. The device also includes a passageway with a tube for receiving a catheter. The device requires insertion of the body portion into the vagina, and also, requires a separate device for taking measurements to size the device to be used by a particular patient.

Another prior art device is disclosed in U.S. Pat. No. 5,653,700 to Byrne et al. The device disclosed by Byrne et al. is suggested for use in assisting in self-catheterization by a female and has a folding perforated catheter attached to a handle. The device disclosed by Byrne et al. uses a self contained perforated catheter and is not designed for use in assisting with the insertion of a standard catheter.

Yet another prior art device that is designed for use by females to assist in self-catheterization is disclosed in U.S. Pat. No. 6,544,240 to Borodulin et al. The device disclosed by Borodulin et al. includes a hub portion and a suction cup having a mirror-like film attached thereto. Borodulin et al. discloses that the female should use the mirror to locate the urethra and to align the hub portion of the device with the urethra so that the catheter can be inserted in the urethra through the hub.

SUMMARY OF THE INVENTION

In one embodiment of the present invention, a device is provided for use in assisting in inserting a catheter in a female. The device includes a main body portion configured to be placed adjacent the pubic bone of a female; a pair of legs extending outwardly from the main body portion; a slot located between the legs; and a flange extending longitudinally along each of the legs.

The flanges may extend along inner sides of the legs adjacent the slot.

The device may also include a catheter guide formed at the upper end of the slot. The catheter guide may include a curved surface that extends along a portion of the main body portion and each of the legs.

The device may further include a gripping portion at an upper end of the main body portion. The gripping portion may includes a tongue-like projection extending from the upper end of the main body portion.

In one embodiment, the main body defines a plane and the legs may extend at a slight angle to the plane. A portion of the flanges may extend substantially transverse to the plane defined by the main body portion.

In one embodiment of the present invention, a device is provided for use in assisting in inserting a catheter into a female wherein the device includes a main body portion configured to be placed adjacent the pubic bone of a female, a pair of flanges connected to the main body portion that are configured to spread the labia of the female, and a catheter guide located between the flanges.

The catheter guide may include a curved surface.

The main body portion may define a plane and further include legs that extend at an angle to the plane of the main body portion. The flanges may extend longitudinally along the legs. The flanges may also extend along the inner sides of the legs and define a slot therebetween. A portion of the flanges may extend substantially transverse to the plane defined by the main body portion, and the catheter guide may be located at one end of the slot.

The device may consist essentially of a unified body.

The device may also be devoid of a vaginal insert.

In one embodiment of the present invention, a device is provided for use in assisting in inserting a catheter in a female wherein the device includes a main body and a pair of flanges connected to the main body that are configured to spread the labia of the female and wherein the height of the flanges is tapered and reduced at an end of the flanges that is toward the main body. The device may include an opening between the flanges for inserting the catheter.

It is also a feature of the present invention to provide a method of inserting a catheter in a female. The method includes the steps of providing a device having a pair of flanges configured to spread the labia of the female and an opening between the flanges for inserting the catheter; placing the device adjacent the perineum of the female; pressing the device against the labia of the female; drawing the device upward toward the pubic bone of the female to separate the labia and expose the urethra of the female in the opening; and inserting a catheter in the urethra through the opening in the device.

The device used in the method may be devoid a portion that is inserted into the vagina of the female.

The method of inserting a catheter in a female may be performed by the female receiving the catheter for self-catheterization. The device may be grasped on a gripping portion of the device.

BRIEF DESCRIPTION OF THE DRAWINGS

The above-mentioned and other features of this invention will become more apparent and the invention itself will be better understood by reference to the following description of embodiments of the present invention taken in conjunction with the accompanying drawings, wherein.

Figure 1:
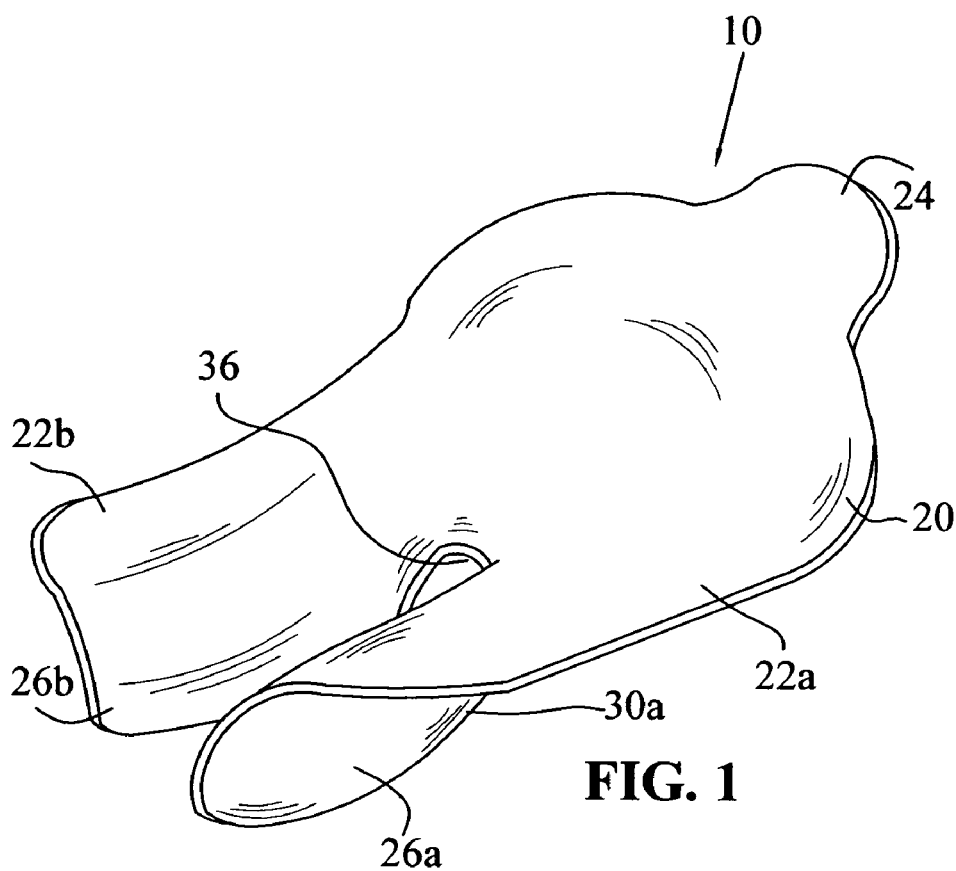
FIG. 1 is a front perspective view of a device in accordance with one embodiment of the present invention for use in assisting in catheterization of a female.
Figure 2:
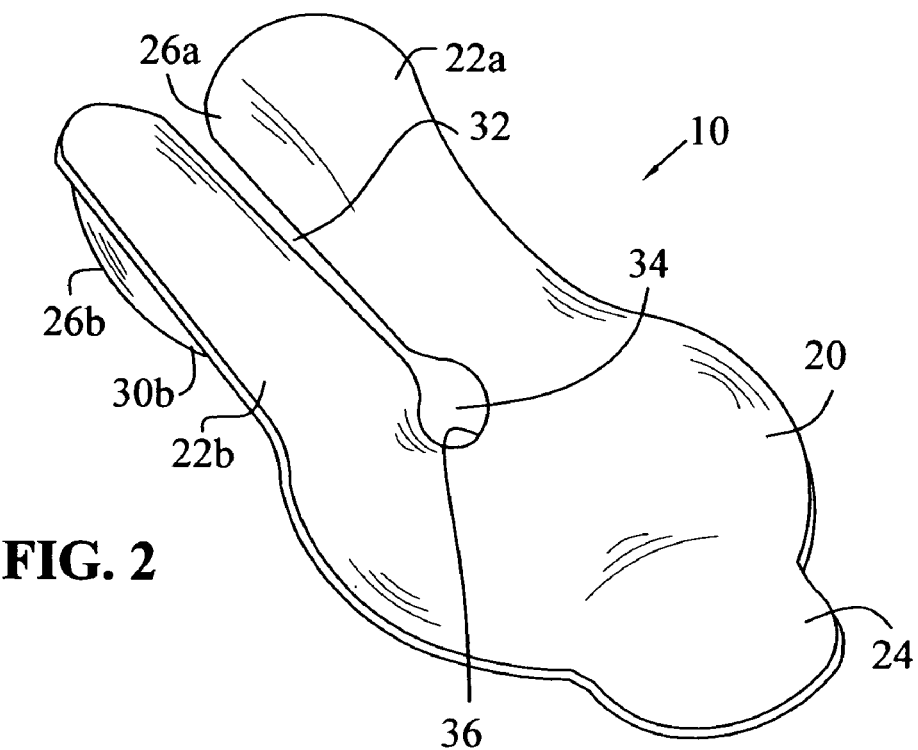
FIG. 2 is a rear perspective view of the device of FIG. 1.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates embodiments of the invention and such exemplifications are not to be construed as limiting the scope of the invention in any manner.

DETAILED DESCRIPTION OF EMBODIMENTS OF THE INVENTION

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

Now referring to FIGS. 1–6, a device for use in assisting in inserting a catheter in a female is shown generally indicated as 10. In the embodiment shown, device 10 is a unitary structure and may be molded from a single piece of material such as a suitable plastic. The device may also be vacuum or thermoformed from a deformable sheet of material; however, the material used to manufacture the device should be relatively rigid when in its final form. Catheterization assist device 10 includes a main body member or portion 20, a pair of legs 22a, 22b, extending from the main body portion and a gripping portion 24 extending from the opposite end of main body portion 20.

Figure 3:
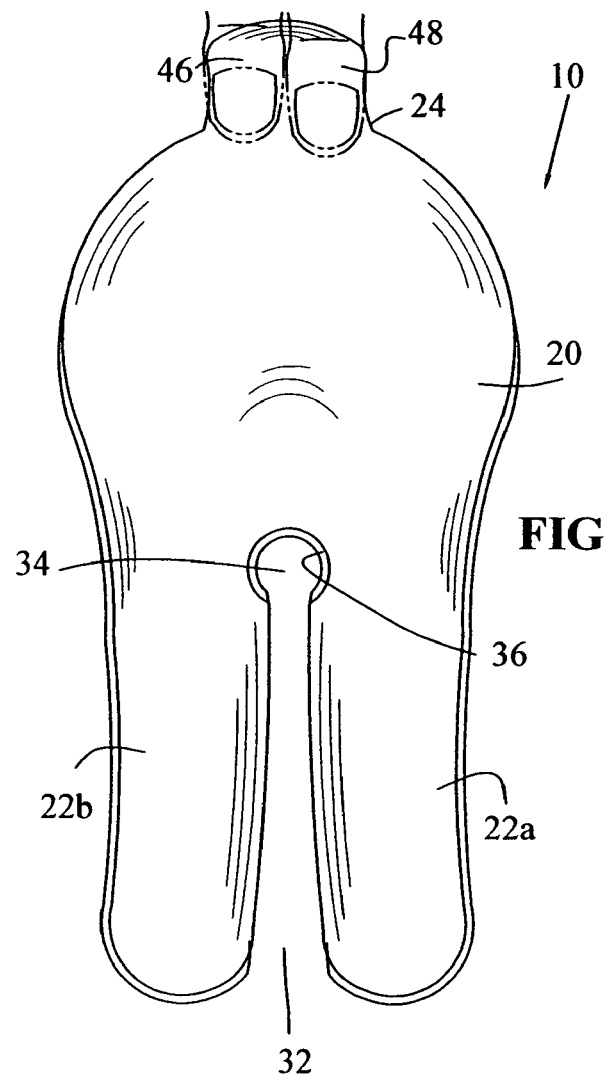
FIG. 3 is a front plan view of the device of FIG. 1.
Figure 4:
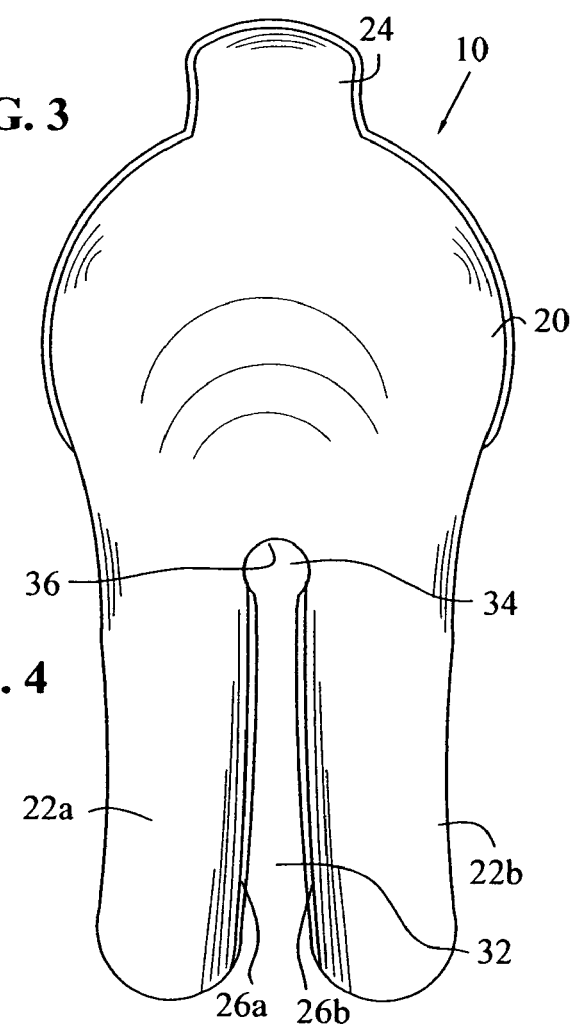
FIG. 4 is a rear plan view of the device of FIG. 1.

In this embodiment, main body portion 20 has a thin generally planar configuration that coincides with the plane of the paper in FIGS. 3 and 4. Legs 22a, 22b extend outward from the main body portion 20 at a slight angle from plane defined by main body portion 20. Legs 22a, 22b, each include a flange 26a, 26b, respectively, extending along the inner sides thereof. Connecting leg 22a to flange 26a and leg 22b to flange 26b are curved portions 28a, 28b, respectively, best shown in FIG. 6. The longitudinal outer edges of flanges 26a, 26b, extend approximately transverse to the plane defined by main body portion 20. The height that flanges 26a, 26b, extend from their respective legs varies along the length of the flanges, and tapered portions 30a, 30b, respectively, are formed at the end of the flanges and reduce the height of the flanges adjacent the body portion for aid in capturing and spreading the labia when used with the method described below. A slot or opening 32 is formed between legs 22a, 22b, and flanges 26a, 26b. In the embodiment shown, slot 32 is open at the lower end of the legs, and a catheter guide 34 is formed at the upper end of the slot where the legs meet main body portion 20. The catheter guide includes an arcuate or curved surface 36 that extends from main body portion 20 around a portion of legs 22a, 22b.

Gripping portion 24 extends from the opposite end of main body portion 20 from legs 22a, 22b. In this embodiment, gripping portion 24 is a thin tongue-like protrusion that is suitable for gripping between the thumb and forefingers for use in the method described below.

Figure 5:
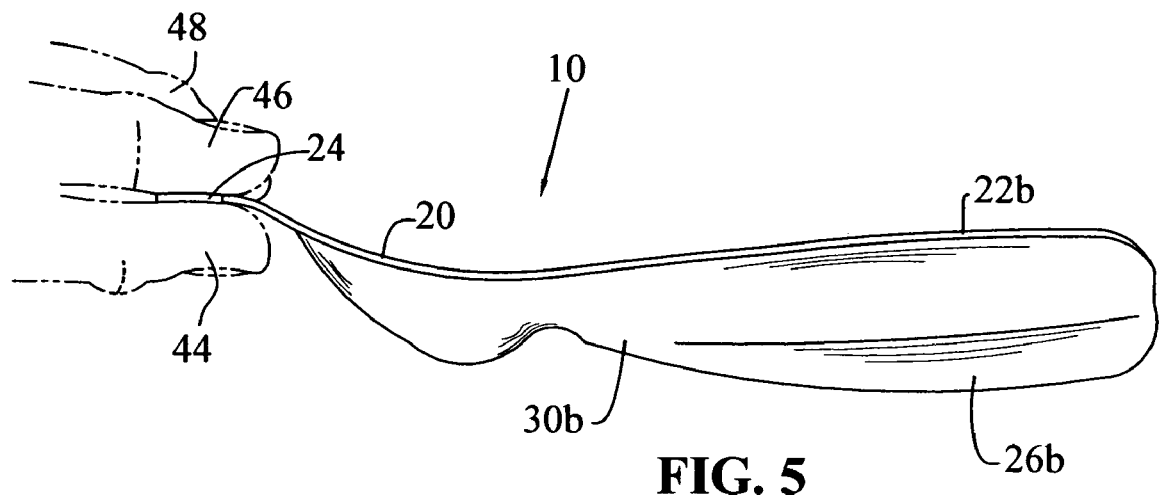
FIG. 5 is a side view of the device of FIG. 1.
Figure 6:
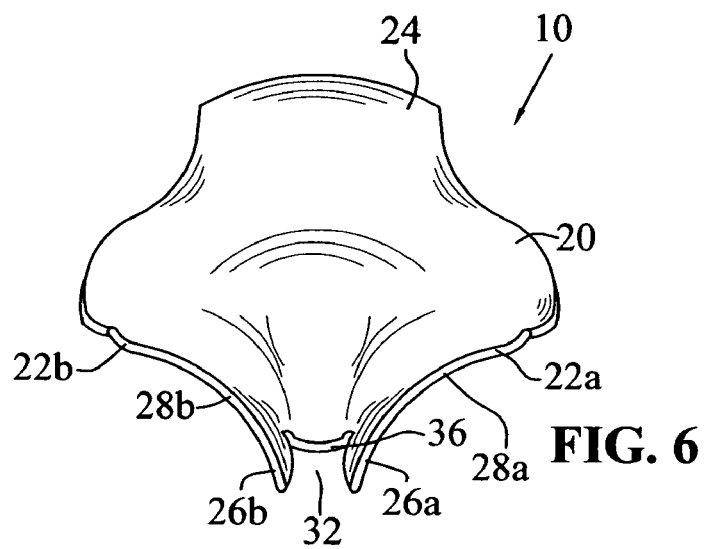
FIG. 6 is an end view of the device of FIG. 1.
Figure 7:
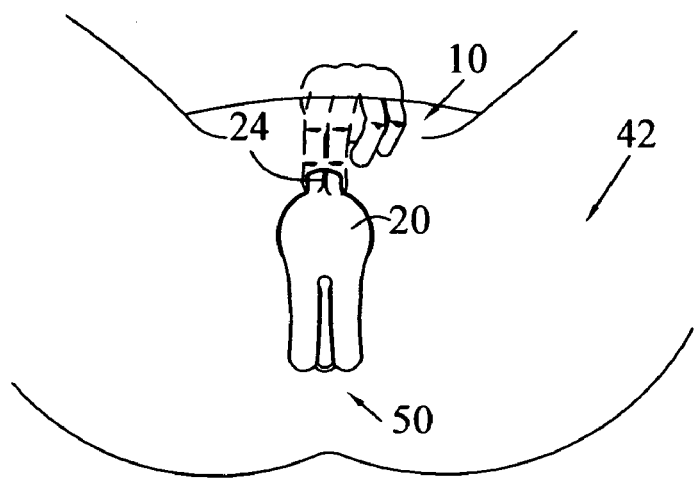
FIG. 7 is front view showing the device of FIG. 1 being placed on a patient before inserting the catheter.
Figure 7A:
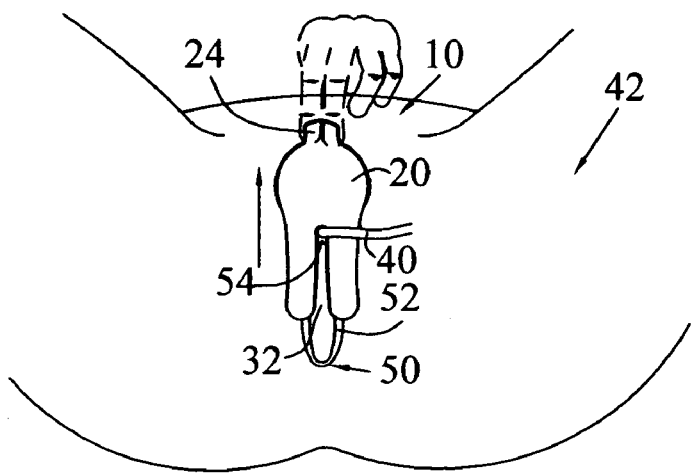
FIG. 7A is a front view showing the device of FIG. 1 being lifted and the catheter inserted.
Figure 8:
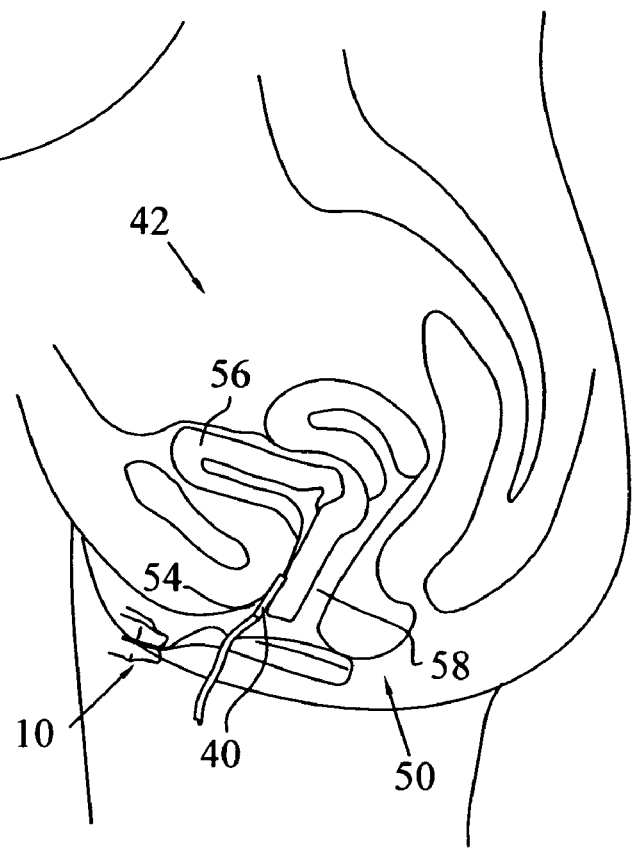
FIG. 8 is a side anatomical view of the device of FIG. 1 being used on a patient.

Now referring to FIGS. 7, 7A and 8, device 10 is shown in use for inserting a catheter 40 in a female patient generally indicated as 42. It should be appreciated that device 10 may be used to assist in inserting a catheter by caregivers of patient 42 or patient 42 may use device 10 for self-catheterization. To use device 10, it is grasped on gripping portion 24 between fingers and/or thumbs 44, 46 and 48 (FIGS. 3 and 5). Device 10 is then placed adjacent the perineum 50 of patient 42 as shown in FIG. 7. Next, device 10 is moved to the position shown in FIG. 7A, by gently pressing it in against the labia 52 and drawing it upward so that main body portion 20 is over the pubic bone in the position shown. As device 10 is drawn upward, flanges 26a, 26b will separate the labia, and the urethra 54 will become exposed at the top of opening 32 within catheter guide 34. It should also be appreciated as seen in FIGS. 7, 7A and 8 that when device 10 is being used, main body portion 20, legs 20a, 20b and the longitudinal length of the flanges 22a, 22b extend generally parallel to the perineum 50 and perpendicular to the urethra canal 54 of the user. In addition, the width of flanges 22a, 22b extending away from the legs 20a, 20b extends generally perpendicular to the perineum 50 and generally parallel to the urethra canal 54.

At this point, catheter 40 can be inserted into the urethra using the other hand (not shown) so as to provide a drainage conduit for bladder 56. It should be appreciated that the configuration of catheter guide 34 can be used to assist in guiding the catheter into the urethra. Catheter 40 may be steadied during insertion by using curved surface 36 of catheter guide 34 as a rest/guide for use in aligning the catheter with the urethra. When the catheter is fully inserted, device 10 can be removed by gently pulling it out and up so that flanges 26a, 26b are no longer pulling the labia apart. Catheter 40 can be left in place while removing device 10 since the catheter can fit through slot 32 as legs 22a, 22b are pulled from around the catheter.

It should be appreciated that the above procedure can be performed without the need to insert any part of device 10 internally in the vagina 58. As seen in FIG. 8, device 10 extends transverse to vagina 58 and is located completely on the exterior thereof.

Figure 9:
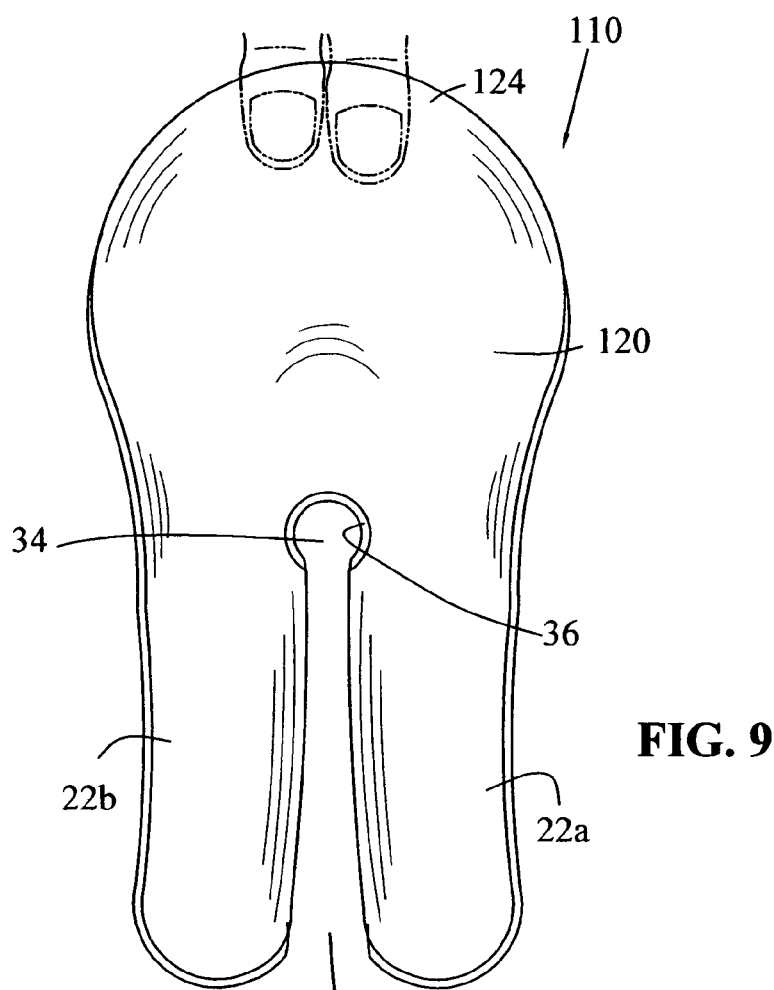
FIG. 9 is a front plan view of another embodiment of the device for use in assisting in catheterizations.
Figure 10:
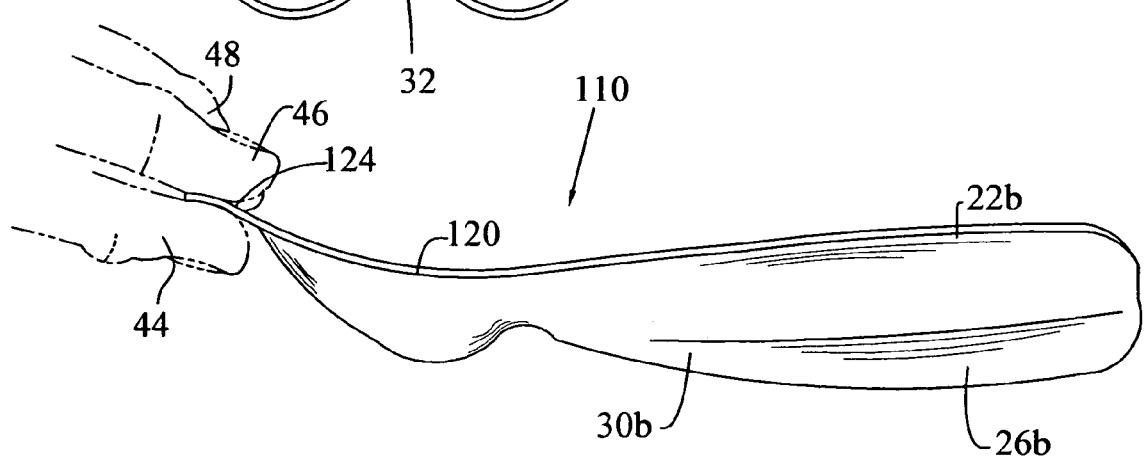
FIG. 10 is a side view of the device of FIG. 9 for use in assisting in catheterizations.

Now referring to FIGS. 9 and 10, another device for use in assisting in inserting a catheter in a female is generally indicated as 110. Device 110 is similar in most respects to device 10 except the main body portion 120 on device 110 has a gripping portion 124 that is coincident with the shape of body portion 120 and does not have a separate tongue-like protrusion. The same procedure can be used to insert catheter 40 with device 110 as is used for device 10.

While the invention has been taught with specific reference to the above embodiments, one skilled in the art will recognize that changes can be made in form and detail without departing from the spirit and scope of the invention. For example, the catheterization assist device may be made from materials other than plastic. For example, a suitable metal may be stamped or otherwise formed into the desired configuration. Additionally, although a unitary design offers certain manufacturing efficiencies, it is also possible to make the device out of multiple parts that may be adhered or otherwise joined together. Also, although slot 32 is shown open at the outer end of the legs, it would be possible to close this end of the device without impairing the function. Furthermore, the general shape of the main body and legs could be varied to any configuration suitable for performing the above described procedure. As such, the described embodiments are to be considered in all respects as illustrative only and not restrictive. The scope of the invention is, therefore, indicated by the following claims rather than by the description or drawings.

What is claimed is:

1. A device for use in assisting in inserting a catheter in a female including:
   a main body portion configured to be placed adjacent the pubic bone of a female;
   a pair of legs extending outwardly from the main body portion;
   a slot located between the legs; and
   a flange extending longitudinally along each of the legs.

2. The device as set forth in claim 1, wherein the flanges extend along inner sides of the legs adjacent the slot.

3. The device as set forth in claim 1, further including a catheter guide at an upper end of the slot.

4. The device as set forth in claim 3, wherein the catheter guide includes a curved surface that is defined by a lower portion of the main body and the legs.

5. The device as set forth in claim 4, wherein the curved surface extends along a portion of the main body member and each of the legs.

6. The device as set forth in claim 1, further including a gripping portion at an upper end of the main body.

7. The device as set forth in claim 6, wherein the gripping portion includes a tongue-like projection extending from the upper end of the main body portion.

8. The device as set forth in claim 1, wherein the main body portion defines a plane and the legs extend at an angle to the plane.

9. The device as set forth in claim 8, wherein at least a portion of the flanges extend substantially transverse to the plane defined by the main body portion.

10. A device for use in assisting in inserting a catheter into a female including:
    a main body portion configured to be placed adjacent the pubic bone of a female;
    a pair of flanges connected to the main body portion configured to spread the labia of the female; and
    a catheter guide located between the flanges.

11. The device as set forth in claim 10, wherein the catheter guide includes a curved surface.

12. The device as set forth in claim 10, wherein the main body portion defines a plane, and the device further includes legs that extend outwardly at an angle to the plane, and wherein the flanges extend longitudinally along the legs.

13. The device as set forth in claim 12, wherein the flanges extend along the inner sides of the legs and define a slot therebetween.

14. The device as set forth in claim 13, wherein a portion of the flanges extend substantially transverse to the plane defined by the main body portion and the catheter guide is located at one end of the slot.

15. The device as set forth in claim 10, consisting essentially of a unified body.

16. The device as set forth in claim 10, wherein the device is devoid of a vaginal insert.

17. A device for use in assisting in inserting a catheter in a female including:
    a main body portion;
    a pair of flanges connected to the main body portion configured to spread the labia of the female, the flanges having a height that is tapered and reduced at an end of the flanges nearest the main body portion; and
    an opening between the flanges for inserting the catheter.

18. A method of inserting a catheter in a female including the steps of:
    providing a device having a pair of flanges configured to spread the labia of the female and an opening between the flanges for inserting the catheter;
    placing the device adjacent the perineum of the female;
    pressing the device against the labia of the female;
    drawing the device upward toward the pubic bone of the female to separate the labia with the flanges and expose the urethra of the female in the opening; and
    inserting a catheter in the urethra through the opening in the device.

19. The method of inserting a catheter in a female as set forth in claim 18, wherein the device is devoid of a portion that is inserted into the vagina of the female.

20. The method of inserting a catheter in a female as set forth in claim 18, wherein the steps may be performed by the female receiving the catheter for self-catheterization.

21. The method of inserting a catheter in a female as set forth in claim 20, wherein the device includes a gripping portion.

22. The device as set forth in claim 1, wherein the main body portion and the legs are configured to be placed parallel with the perineum of the female and perpendicular to the urethra canal.

23. The device as set forth in claim 22, wherein the longitudinal length of the flange is configured to be placed parallel with the perineum and perpendicular to the urethra canal and the width of the flange is configured to extend generally perpendicular to the perineum and parallel to the urethra canal.

24. The device as set forth in claim 10, wherein the main body portion is configured to be placed generally parallel to the perineum and perpendicular to the urethra canal of the female, and the longitudinal length of the flange is configured to be placed parallel with the perineum and perpendicular to the urethra canal and the width of the flange is configured to extend generally perpendicular to the perineum and parallel to the urethra canal.

25. The device as set forth in claim 17, wherein the longitudinal direction of the flanges extends generally parallel to the perineum and perpendicular to the urethra canal of the female.

26. The method as set forth in claim 18, wherein the longitudinal direction of the flanges extends generally parallel to the perineum and perpendicular to the urethra canal of the female.

* * * * *